(12) United States Patent
Hamakubo et al.

(10) Patent No.: US 7,329,509 B2
(45) Date of Patent: Feb. 12, 2008

(54) METHOD FOR EXPRESSING A FUNCTIONAL MEMBRANE-BOUND RECEPTOR PROTEIN USING BUDDED BACULOVIRUS

(75) Inventors: Takao Hamakubo, Tokyo (JP); Tatsuhiko Kodama, Tokyo (JP); Hiroshi Itoh, Nara (JP); Kazuyuki Masuda, Tokyo (JP)

(73) Assignee: Toudai TLO, Ltd., Tokyo (JP)

( * ) Notice: Subject to any disclaimer, the term of this patent is extended or adjusted under 35 U.S.C. 154(b) by 107 days.

(21) Appl. No.: 10/167,411

(22) Filed: Jun. 13, 2002

(65) Prior Publication Data

US 2007/0287146 A1    Dec. 13, 2007

(30) Foreign Application Priority Data

Aug. 16, 2001 (JP) ............................. 2001-246977

(51) Int. Cl.
*G01N 33/567* (2006.01)
(52) U.S. Cl. ............................. 435/69.1; 435/5; 435/7.2
(58) Field of Classification Search ................... 435/5, 435/7.2, 69.1; 436/501
See application file for complete search history.

(56) References Cited

U.S. PATENT DOCUMENTS

| 5,861,279 | A | * | 1/1999 | Zhang et al. | ............... | 435/69.1 |
| 6,713,278 | B1 | * | 3/2004 | Bouvier et al. | ............ | 435/69.1 |
| 2002/0052040 | A1 | | 5/2002 | Hunt | | |

FOREIGN PATENT DOCUMENTS

| EP | 1219705 | 7/2002 |
| WO | 98/46777 | 10/1998 |
| WO | 01/02551 | 1/2001 |

OTHER PUBLICATIONS

Butkerait et al. Expression of the Human 5-Hydroxytryptamine 1A Receptor in SF9 Cells. Aug. 4, 1995, J. Biol. Chem. 270(31):18691-18699.*
Grunewald et al. In Vivo Reconstitution of Depomine D2s Receptor-Mediated G Protein Activation in Baculovirus-Infected Inse Cells: Preferred Coupling to Gi1 versus Gi2. 1996, Biochemistry 35(48):15162-15173.*
Yolande Cordeaux et al., "Agonist Regulation of $D_2$ Dopamine Receptor/G Protein Interation, The Journal of Biological Chemistry", vol. 276, No. 31, pp. 28667-28675 (2001).
Bart J.B. Francken et al., "Human 5-Hydroxytryptamine$_{5A}$ Receptors Activate Coexpressed $G_i$ and $G_o$ Proteins in *Spodoptera frugiperda* 9 Cells ", Molecular Pharmacology, vol. 57, pp. 1034-1044 (2000).
Tae Weon Lee et al., "Restricting the Mobility of $G_5\alpha$: Impact on Receptor and Effector Coupling", Biochemistry, vol. 38, pp.13801-13809 (1999).
Monika Raab et al., "The T-Cell Antigen CD5 Acts as a Receptor and Substrate for the Protein-Tyrosine Kinase p. $56^{lck}$", Molecular and Cellular Biology, vol. 14, No. 5, pp. 2862-2870 (1994).
Nicola Gargano et al., "Modulation of Nerve Growth Factor Internalization by Direct Interaction Between p75 and TrkA Receptors", Journal of Neuroscience Research, vol. 50, pp. 1-12 (1997).
Thomas P. Loisei et al., "Recovery of Homogeneous and Functional $\beta_2$-adrenergic Receptors form Extracellular Baculovirus Particles", Nature Biotechnology, vol. 15, pp. 1300-1304 (1997).
Christopher G. Tate et al., "Heterologous Expression of G-protein-coupled Receptors", TIBTECH, vol. 14, pp. 426-430 (1996).
R. Grisshammer et al., "Overexpression of Integral Membrane Proteins for Structural Studies", Quarterly Reviews of Biophysics, vol. 28, No. 3, pp. 315-422 (1995).
Thomas P. Loisel et al., "Recovery of Homogeneous and Functional $\beta_2$-adrenergic Receptors from Extracellular Baculovirus Particles", Nature Biotechnology, vol. 15, pp. 1300-1304 (1997).
G. Ishihara et al., "Expression of Cholesterol Regulatory Proteins on Extracellular Baculoviruses", XIIth International Symposium on Atherosclerosis, Stockholm, Sweden, Jun. 25-29, 2000, Poster Abstracts, pp. 290.
J. Craig Venter et al., "The Sequence of the Human Genome", Science, vol. 291; pp. 1304-1351 (2001).
Toshio Igarashi et al., "Characterization of the Leukotrine $B_4$ Receptor in Porcine Leukocytes: Separation and Reconstitution with Heterotrimeric GTP-Binding Proteins", Eur. J. Biochem., vol. 259, pp. 419-425 (1999).
Daniela Leopoldt et al., "G Proteins Endogenously Expressed in Sf9 Cells: Interactions with Mammalian Histamine Receptors", Naunyn-Schmiedeberg's Arch Pharmacol, Bol. 356, pp. 216-244 (1997).
Christian Heuss et al., "G-Protein-Independent Signaling by G-Protein-Coupled Receptors", Trends Neurosci., vol. 23, pp. 469-475 (2000).
John R. Hepler, "Emerging Roles for RGS Proteins in Cell Signalling", TiPS, vol. 20, pp. 376-382 (1999).
Ulrik Gether, "Uncovering Molecular Mechanisms Involved in Activation of G Protein-Coupled Receptors", Endocrine Reviews, vol. 21, No. 1, pp. 90-113 (2000).
1998 Receptor & Ion Channel Nomenclature Supplement: Trends in Pharmacological Science.

(Continued)

*Primary Examiner*—John Ulm
(74) *Attorney, Agent, or Firm*—Greenblum & Bernstein, P.L.C.

(57) ABSTRACT

The object of the present invention is to develop a technique for expressing a functional membrane-bound protein by using baculovirus and insect cell expression system. The present invention provides a method for expressing a functional membrane-bound receptor protein which comprises steps of culturing a host infected with at least one type of recombinant baculovirus which contains a gene encoding an interacting protein and a gene encoding a membrane-bound receptor protein which interacts with said interacting protein to perform its function, and co-expressing said interacting protein and said membrane-bound receptor protein in a budded baculovirus released from said host.

7 Claims, 8 Drawing Sheets

OTHER PUBLICATIONS

Charles N. Serhan et al., "Lipid Mediator Networks in Cell Signaling: Update and Impact of Cytokines", FASEB Journal, vol. 10, pp. 1147-1157 (1996).

Takehiko Yokomizo et al., "Leukotrine $B_4$ Receptor: Cloning and Intracellular Signaling", Am. J. Respir, Care Med., vol. 161, pp. S51-S55 (2000).

Takehiko Yokomizo et al., "A G-Protein-Coupled Receptor for Leukotriene $B_4$ that Mediates Chemotaxis", Nature, vol. 387, pp. 620-624 (1997).

Remi Gaudreau et al., "Signalling Through the Leukotrine $B_4$ Receptor Involves both $\alpha_i$ and $\alpha_{16}$, but not $\alpha_q$ or $\alpha_{11}$ G-Protein Subunits", Biochem., J., vol. 335, pp. 15-18 (1998).

Louis A. Obosi et al., "Functional Characterisation of the *Drosophila* 5-$HT_{dro1}$ an 5-$HT_{dro2B}$ Serotonin Receptors in Insect Cells: Activation of a $G_{as}$-like Protein by 5-$HT_{dro1}$ but Lack of Coupling to Inhibitory G-Proteins by 5-$HT_{dro2B}$", FEBS Letters, vol. 381, pp. 233-236 (1996).

M. Bouvier et al., "Expression and Recovery of Functional G-Protein-Coupled Receptors Using Baculovirus Expression Systems," Current Opinion in Biotechnology, vol. 9, No. 5, Oct. 1998, pp. 522-527.

R. A. Figler et al., "Reconstitution of Recombinant Bovine $A_1$ Adenosine Receptors in Sf9 Cell Membranes with Recombinant G Proteins of Defined Composition," Molecular Pharmacology, vol. 50, No. 6, 1999, pp. 1587-1595.

K. Masuda et al., "A Combinatorial G Protein-Coupled Receptor Reconstitution System on Budded Baculovirus. Evidence for Galphai and Galphao Coupling to a Human Leukotriene B4 Receptor," Journal of Biological Chemistry, vol. 278, No. 27, Jul. 4, 2003, pp. 24552-24562.

R. Brys et al., "Reconstitution of the Human 5-$HT_{1D}$ Receptor-G-Protein Coupling: Evidence for Constitutive Activity and Multiple Receptor Conformations", Molecular Pharmacology, (2000), vol. 57, pp. 1132-1141.

* cited by examiner

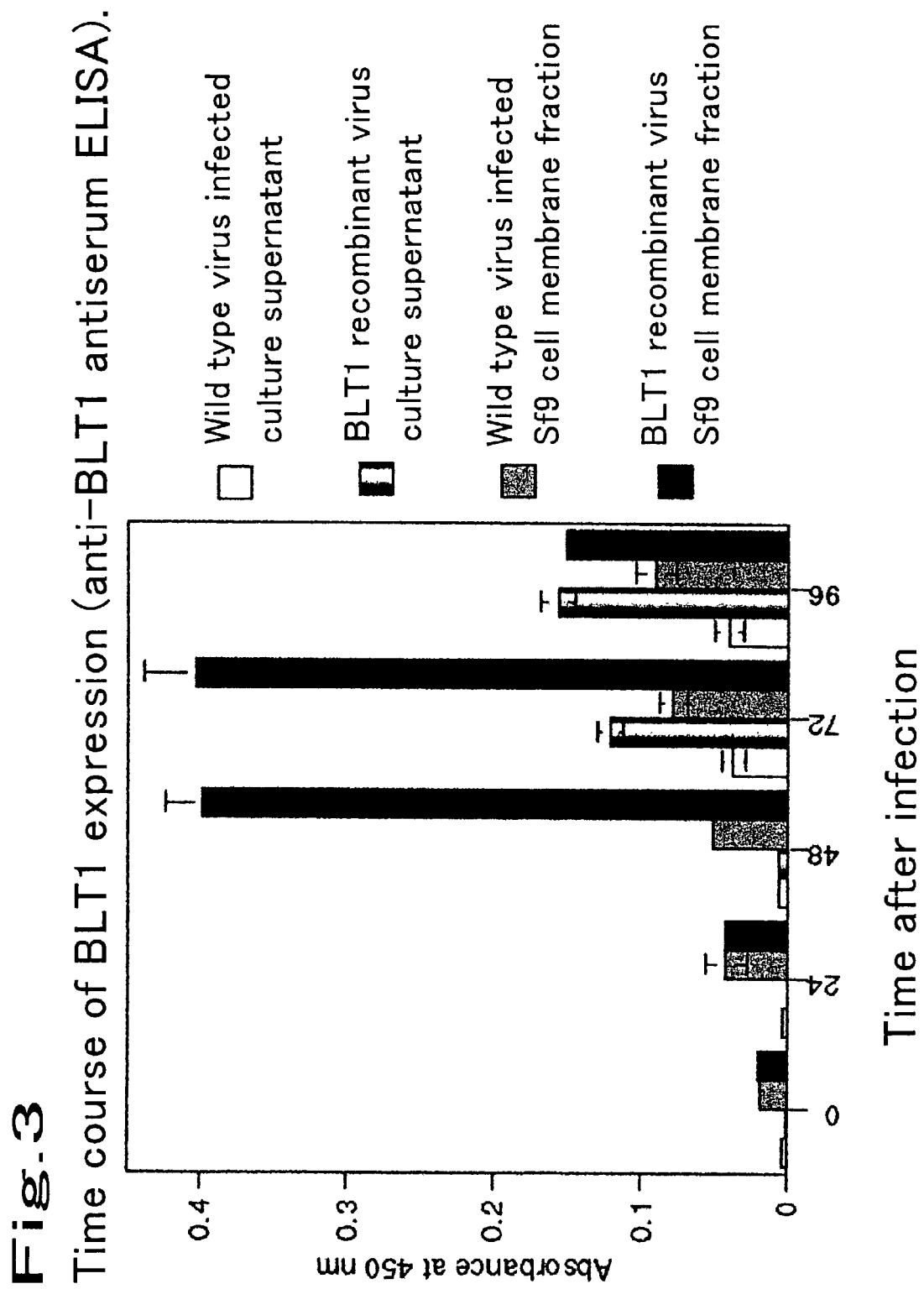

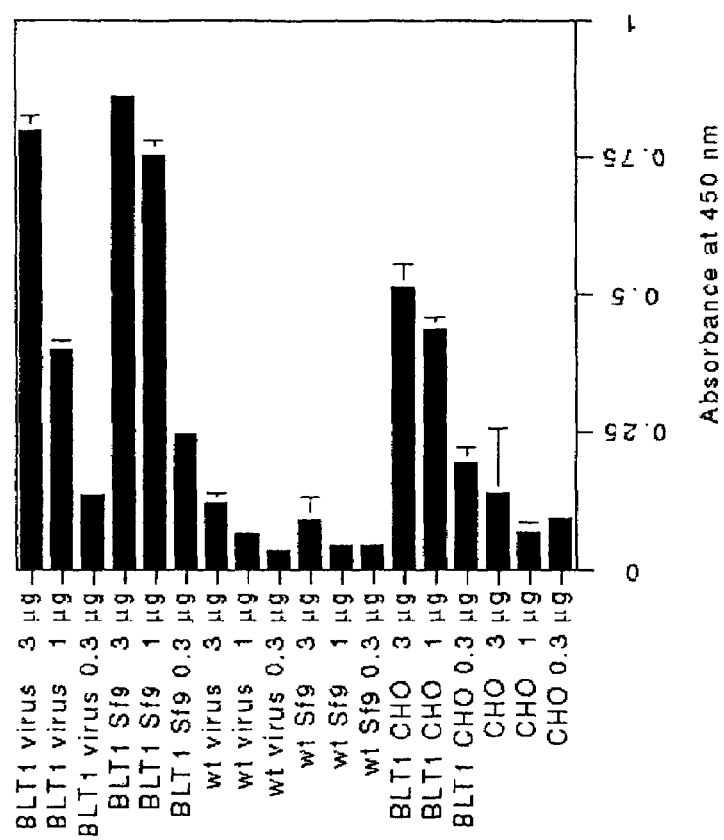
Fig. 4 Comparison of BLT1 expression amount (anti BLT1 antibody ELISA)
BLT1 virus: BLT1 expressing BV fraction
BLT1 Sf9: BLT1 expressing Sf9 cells membrane fraction
wt virus: wild type BV fraction
wt Sf9: wild type Sf9 cells membrane fraction
BLT1 CHO: BLT1 expressing CHO (chinese hamster ovary) cells membrane fraction
CHO: CHO cells membrane fraction

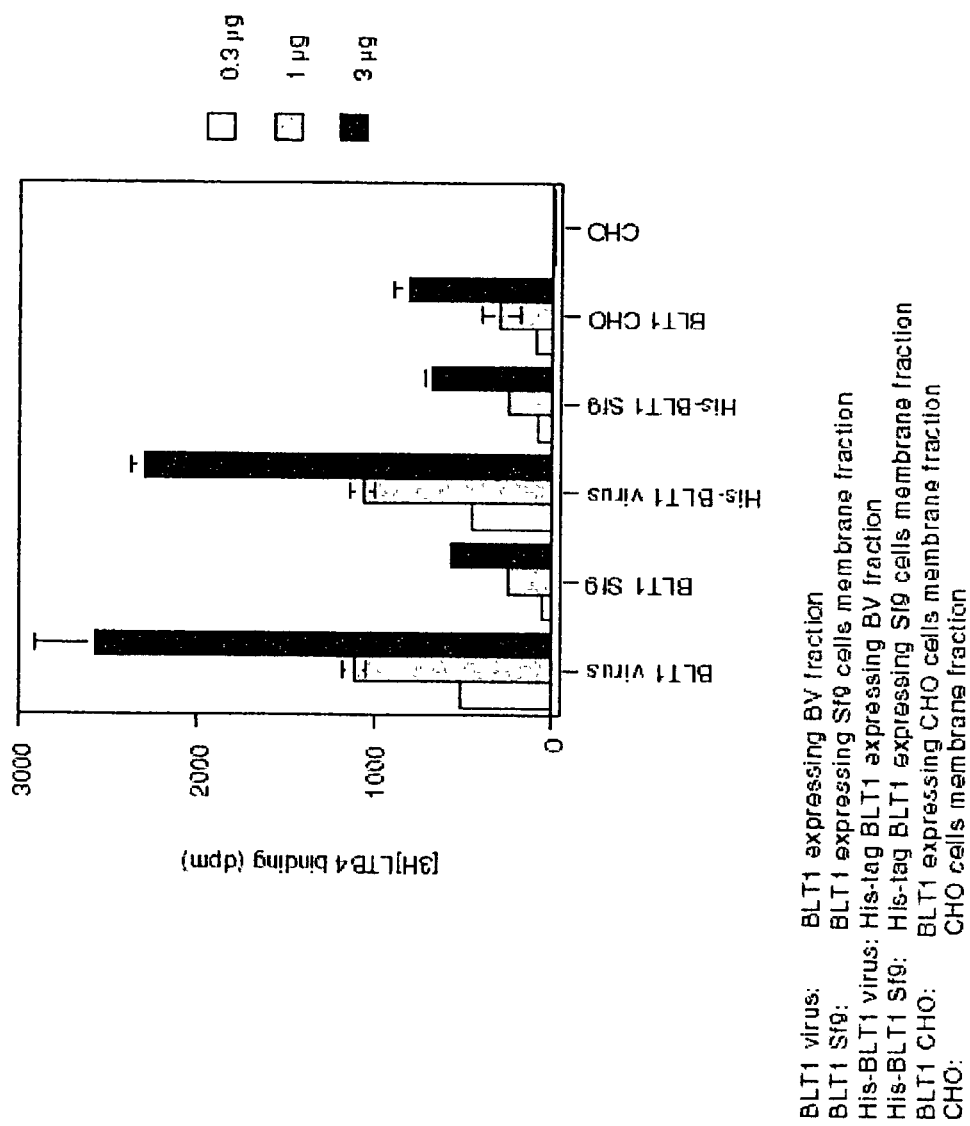
Fig. 5 Comparison of binding activities of the leukotriene B4 receptor (LTB4)

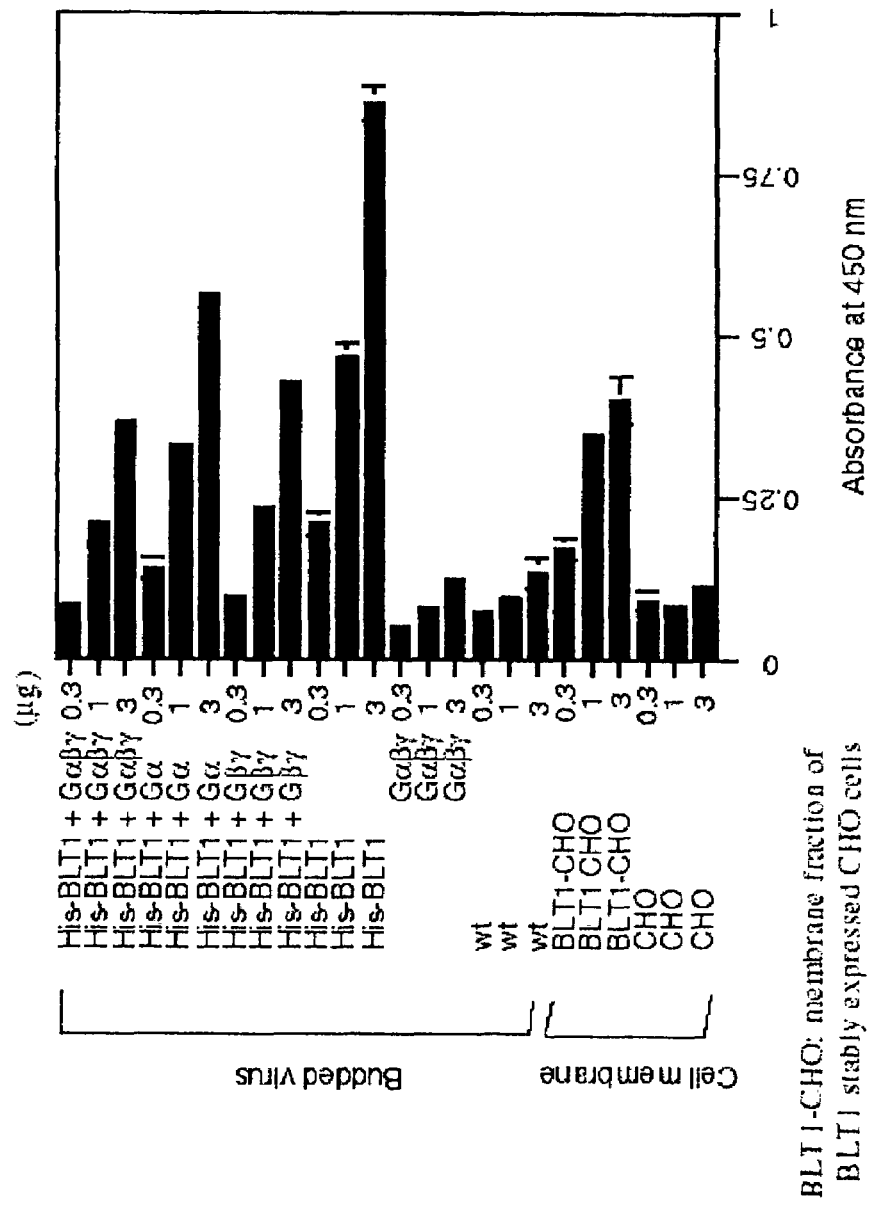

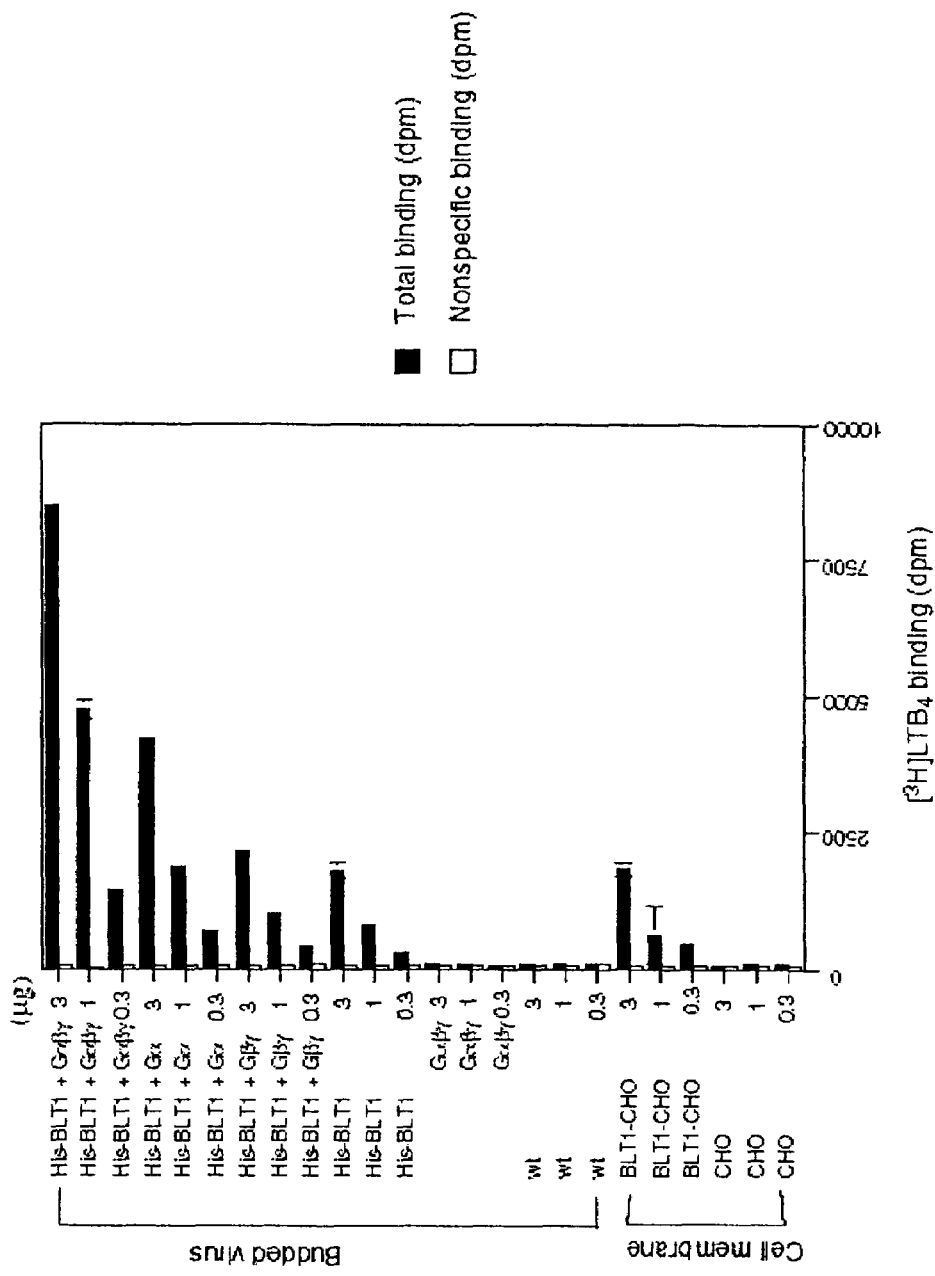

Fig. 8 [³H] LTB₄ binding activity in budded virus which co-expresses BLT1 and various G protein

METHOD FOR EXPRESSING A FUNCTIONAL MEMBRANE-BOUND RECEPTOR PROTEIN USING BUDDED BACULOVIRUS

TECHNICAL FIELD

The present invention relates to a method for expressing a functional membrane-bound receptor protein using a budded baculovirus. More particularly, the present invention relates to a method for expressing a functional membrane-bound receptor protein wherein an interacting protein and a membrane-bound receptor protein are co-expressed in the budded baculovirus released from a host.

BACKGROUND OF THE INVENTION

A baculovirus expression system enables high-level expression of a gene of interest by causing recombination of the gene in Sf9 cells using a promoter of a polyhedrin gene of baculovirus. A polyhedrin is expressed in the nucleus of Sf9 cell at a high level as an occlusion body which is a form to be used when viruses become latent within the cell. The baculovirus expression system where a recombinant protein is introduced into a polyhedrin gene and the expressed proteins are purified, has many advantages over that of *Escherichia coli* or yeast, such that the expressed proteins having a lot of hydrophobic regions such as membrane-bound proteins are comparatively hard to agglutinate and the expressed proteins undergo a posttranscriptional modification which is necessary for protein functions, such as addition of sugar chains and coordination of metal ion, and therefore the baculovirus expression system is often used as an expression system of membrane receptor protein (Tate C G, Grisshammer R., Trends in Biotechnology 1996, 14, pp 426-430, Heterologous expression of G protein-coupled receptors; and, Grisshammer R, Tate C G, Quarterly Reviews of Biophysics 1995, 28, pp 315-422, Overexpression of integral membrane proteins for structural studies).

Baculovirus has another life cycle in addition to that a baculovirus becomes a polyhedrin virus coated with polyhedrin and present in the nucleus. In order to proliferate and infect, baculovirus becomes a budded virus (Budded virus: this is also referred to as budded baculovirus in this specification), rupturing Sf9 cell membrane and being released outside the cell. Loisel et al have reported that at this time a receptor of seven-transmembrane type recombined into the above polyhedrin protein is expressed on the cell membrane and recovered from the envelope of the budded baculovirus (Loisel T P, Ansanay H, St-Onge S, Gay B, Boulanger P, Strosberg A D, Marullo S, Bouvier M., Nat Biotechnol. 1997 November; 15(12): 1300-4., Recovery of homogeneous and functional beta 2-adrenergic receptors from extracellular baculovirus particles). It has also been reported that, whereas most receptors of seven-transmembrane type expressed in a host cell have a sugar chain structure which is not functional, only functional receptors are recovered from the viral envelope.

It has also been reported that a group of proteins which are present in endoplasmic reticulum (ER) membrane or Golgi apparatus membrane and are involved in the intracellular cholesterol feedback regulation, such as SREBP (sterol regulatory element binding protein)2, HMG-CoA (hydroxymethyl glutaryl coenzyme A) reductase, SCAP (SREBP cleavage activating protein), S1P (site 1 protease), are expressed on the virus envelope with maintaining their functions (Ishihara, G, Shirai, H., Yamaguchi, M., Fukuda, R., Hamakubo, T., and Kodama, T., Atherosclerosis, 151, p 290, 2000, Expression of cholesterol regulatory proteins on extracellular baculoviruses).

On the other hand, G protein coupled receptors (GPCRs) are important as a target for development of medicament, and about 700 receptors are reported in the genome database (Venter J G, Adams M D, Myers E W, et al., Science 291, pp 1304-1351, 2001, The sequence of the human genome). The mechanism of the signal transduction of hormone has also been studied (Tate C G, Grisshammer R., Trends in Biotechnology 1996, 14, pp 426-430, Heterologous expression of G protein-coupled receptors). GPCR has seven transmembrane domains, and is coupled with heterotrimeric G protein. The type of α subunit of G protein which is bond (coupled) when binding with ligand is determined depending on the type of receptor. For example, in the case of the leukotriene B4 receptor, it is Gi or Gq class G protein (Igarashi T, Yokomizo T, Tsutsumi O, Taketani Y, Shimizu T and Izumi T., Eur. J. Biochem., 259, pp 419-425, 1999, Characterization of the leukotriene B4 receptor in porcine leukocytes Separation and reconstitution with heterotrimeric GTP-binding proteins). It is known that, in the case of adrenaline receptor, Gs is coupled. According to the report of Loisel et al, Gs from Sf9 cells is expressed and coupled to form a complex on a budded virus (Loisel T P, Ansanay H, St-Onge S, Gay B, Boulanger P, Strosberg A D, Marullo S, Bouvier M., Nat Biotechnol. 1997, November 15(12), pp 1300-1304, Recovery of homogeneous and functional beta 2-adrenergic receptors from extracellular baculovirus particles). Various isoforms of G protein are expressed in Sf9 cells as in mammal cells, but its amounts are different depending on the type of G protein (Leopoldt D, Harteneck C, Numberg R, Naunyn-Schmiedeberg's Arch Pharmacol, 356, pp 216-224, 1997, G Proteins endogenously expressed in Sf9 cells: interactions with mammalian histamine receptors). Since Gs is relatively abundantly present in Sf9 cells, adrenaline receptor expressed in the virus can be couple with Gs from insect cells so that a functional membrane receptor is expressed in the system of Loisel et al. However, in the case of the receptor (for example, leukotriene B4 receptor) which is coupled with other Gα isoform such as Gi which is relatively poor in Sf9 cells, it is difficult to obtain a functional receptor having a high affinity if it is expressed.

SUMMARY OF THE INVENTION

An object of the present invention is to solve the aforementioned problems. Thus, the object of the present invention is to develop a technique for expressing a functional membrane-bound protein by using baculovirus and insect cell expression system.

The present inventors have earnestly studied to achieve the above objects. As a result, they have succeeded in obtaining a high affinity receptor by preparing a virus which expresses a receptor protein and G protein subunits, and reconstituting the protein on a budded virus.

Namely, also in the case of G protein such as Gi which is poor in Sf9 cells, by infecting insect cells with a virus having integrated genes of each of α, β and γ subunits together with a recombinant virus of the receptor, the expressed receptor can form a complex with a heterotrimeric G protein which is integrated in the budded virus, and can have a binding activity of high affinity. There is a problem that, since low affinity receptor is abundantly expresses in the membrane fraction of Sf9 cells which express a complex of receptor and G protein by co-infection, it is difficult to measure only the activity of high affinity receptor. However, it has been unexpectedly found that the binding activity of high affinity can be measured by using a complex of receptor and G protein which is expressed on budded baculovirus. The present invention have been completed based on these findings.

Thus, according to the present invention, there is provided a method for expressing a functional membrane-bound receptor protein which comprises steps of culturing a host infected with at least one type of recombinant baculovirus which contains a gene encoding an interacting protein and a gene encoding a membrane-bound receptor protein which interacts with said interacting protein to perform its function, and co-expressing said interacting protein and said membrane-bound receptor protein in a budded baculovirus released from said host.

Preferably, a host infected with at least one type of recombinant baculovirus which contains a gene encoding an interacting protein and at least one type of recombinant baculovirus which contains a gene encoding a membrane-bound receptor protein which interacts with said interacting protein to perform its function is cultured, and said interacting protein and said membrane-bound receptor protein is co-expressed in a budded baculovirus released from said host.

According to another aspect of the present invention, there is provided a method for preparing a physiologically active membrane-bound receptor protein which comprises steps of culturing a host infected with at least one type of recombinant baculovirus which contains a gene encoding an interacting protein and a gene encoding a membrane-bound receptor protein which interacts with said interacting protein to perform its function, and recovering a budded baculovirus released from said host.

Preferably, a host infected with at least one type of recombinant baculovirus which contains a gene encoding an interacting protein and at least one type of recombinant baculovirus which contains a gene encoding a membrane-bound receptor protein which interacts with said interacting protein to perform its function is cultured, and a budded baculovirus released from said host is recovered.

Preferably, the interacting protein is a coupled protein. Particularly preferably, the interaction protein is G protein, and the membrane-bound receptor protein is G protein coupled receptor protein. Preferably, the host is an insect cell or an insect larva.

According to further another aspect of the present invention, there is provided a budded baculovirus which is released from a host infected with at least one type of recombinant baculovirus which contains a gene encoding an interacting protein and a gene encoding a membrane-bound receptor protein which interacts with said interacting protein to perform its function.

Preferably, the interacting protein is a coupled protein. Particularly preferably, the interaction protein is G protein, and the membrane-bound receptor protein is G protein coupled receptor protein. Preferably, the host is an insect cell or an insect larva.

According to further another aspect of the present invention, there is provided a method for analyzing an interaction between a membrane-bound receptor protein in the budded baculovirus and a ligand, wherein the above budded baculovirus of the present invention is used.

According to further another aspect of the present invention, there is provided a method for screening a substance which promotes or inhibits an interaction between a membrane-bound receptor protein in the budded baculovirus and a ligand, wherein an interaction between a membrane-bound receptor protein in the budded baculovirus and a ligand is analyzed in the presence of a test substance by using the above budded baculovirus of the present invention.

According to further another aspect of the present invention, there is provided a substance which promotes or inhibits an interaction between a membrane-bound receptor protein and a ligand, which is obtained by the above method for screening of the present invention.

BRIEF DESCRIPTION OF DRAWINGS

FIG. 3 shows a time course of BLT1 expression (anti-BLT1 antiserum ELISA).

FIG. 4 shows a comparison of BLT1 expression amount (anti BLT1 antibody ELISA).

FIG. 5 shows a comparison of binding activities of the leukotriene B4 receptor (LTB4).

FIG. 6 shows BLT1 expression on budded virus coinfected with various G protein subunit recombinant viruses (ELISA with anti-BLT1 antiserum).

FIG. 7 shows [$^3$H]LTB$_4$ binding to BV fractions coinfected with HisBLT1 and various G protein subunit recombinant viruses.

FIG. 8 shows [$^3$H]LTB$_4$ binding activity in budded virus which co-expresses BLT1 and various G protein.

DETAILED DESCRIPTION OF THE INVENTION

Figure 1:
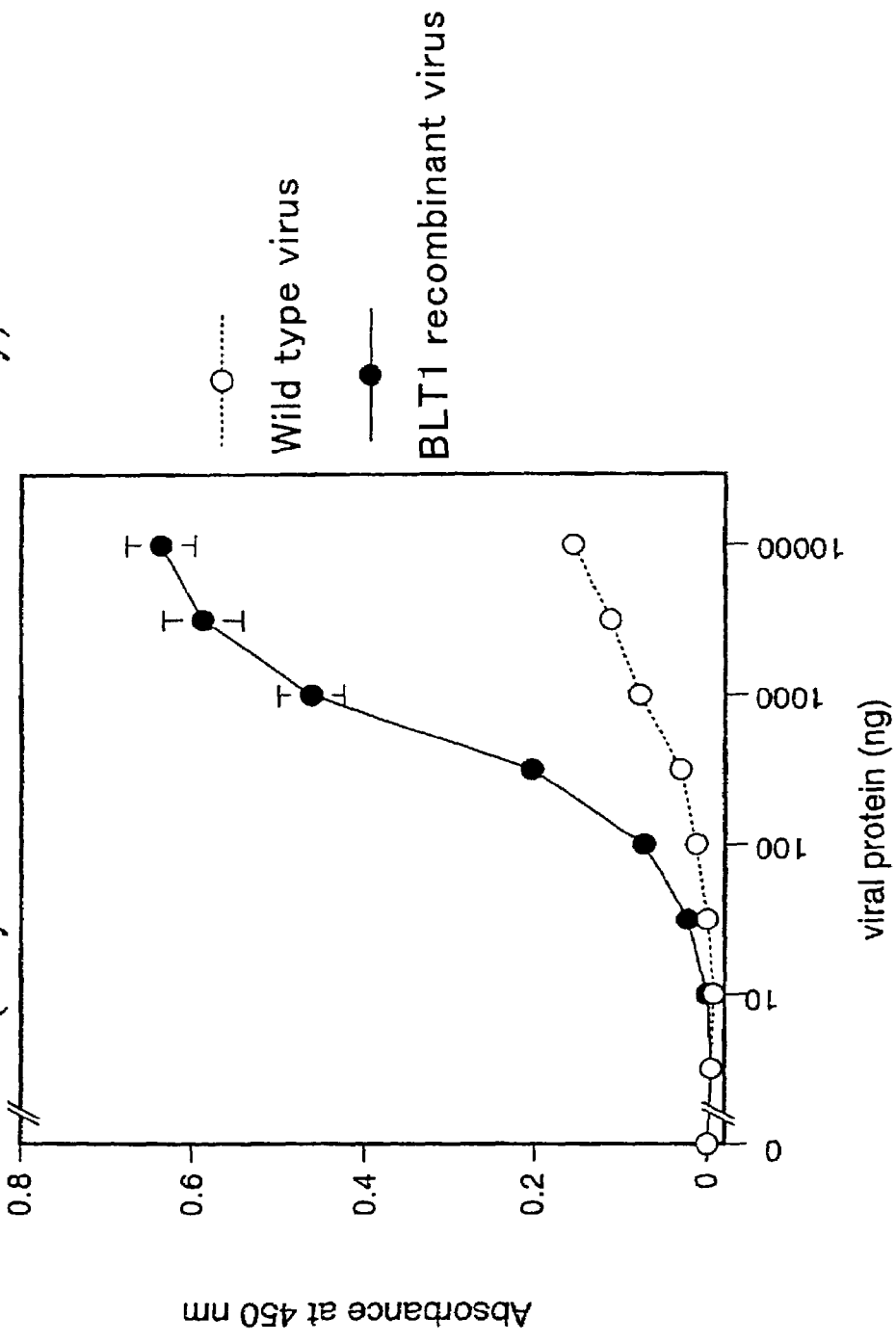
FIG. 1 shows the result of ELISA using anti-BLT1 antiserum in BV fraction.

The embodiments and methods of the present invention will be described below in detail.

The method for expressing a functional membrane-bound receptor protein according to the present invention is characterized in that a host infected with at least one type of recombinant baculovirus which contains a gene encoding an interacting protein and a gene encoding a membrane-bound receptor protein which interacts with said interacting protein to perform its function is cultured, and said interacting protein and said membrane-bound receptor protein are co-expressed in a budded baculovirus released from said host. In the present invention, two types of protein are co-expressed as mentioned above. The genes each of which encodes each of said two types of protein may be contained in single same recombinant baculovirus or may be contained in different baculoviruses. In the present invention, a membrane-bound receptor protein having a physiological activity can be prepared by culturing a host infected with a recombinant baculovirus having genes encoding said two types of protein, and collecting a budded baculovirus released from the host.

The term "membrane-bound" in the present specification broadly refers to a target protein being present on a cell membrane or the plasma membrane of intracellular organelles (for example, endoplasmic reticulum and Golgi apparatus). The term "receptor" in the present specification widely means a protein capable of interacting (binding) with a ligand. Preferably, such a protein is capable of transmitting information resulting from interaction with a ligand, into a cell.

Examples of a membrane-bound receptor protein include 7-transmembrane receptor proteins for hormone, odor, taste, light and the like; LDL receptors; scavenger receptors; 1-transmembrane receptors for growth hormone, insulin, TNFα, glutamic acid and the like; ion channel receptors, such as GABA, acetylcholine and ryanodine; T cell receptors, and Fc receptors. Those proteins can form a complex. Among these proteins, the membrane-bound receptor protein used in the present invention is a protein which functions by interacting with an interacting protein.

Combinations of membrane-bound receptor proteins and interacting proteins are not specifically limited. Examples of such combinations are as follows:

a combination of G protein coupled receptor protein and G protein;

a combination of T cell receptor (α, β, γ, δ chains)/CD3 complexes (γ, δ, ε, ξ, ι chains) and Src family thyrosine kinase, such as Fyn protein;

a combination of B cell receptor and Src family thyrosine kinase such as Lyn, Syk, blk and lck protein; and a combination of Fcγ receptor or Fcε receptor and Src family thyrosine kinase such as Syk, Csk and Lyn proteins.

Examples of interaction of G protein-coupled receptors include coupling of trimeric G proteins with receptor proteins; interaction of $β_2$ adrenaline receptors with β-arrestin or G protein-coupled receptor kinase (GRK); interaction of metabotropic glutamate receptors (mglu) with Homer proteins; and interaction of $β_2$ adrenaline receptors with $Na^+$, $H^+$ exchange factors (Heuss, C. and Gerber, U. G-protein-independent Signaling by G-protein-coupled Receptors. Trends Neurosci. (2000) 23, 469-475).

Other examples of interaction of G protein-coupled receptors include interaction of G proteins or their coupling receptors with a group of proteins (Hepler, J. R. Emerging Roles for RGS Proteins in Cell Signalling. TiPS (1999) 20, 376-382), which have an RGS domain coupling to Gα subunits called RGS (Regulators of G protein signaling) proteins, such as binding of metabotropic glutamate receptors (mglu) with RGS4, and binding of interleukin 8B receptors with RGS12.

Examples of a G protein include a trimeric G protein. Examples of α subunits of G proteins include those of Gs class, such as Gsα and Golfα; Gi class, such as Gi1α, Gi2α, Gi3α, Go1α, Go2α, Gt1α, Gt2α and Ggustα; Gq class, such as Gqα, G11α, G14α, G15α and G16α; and G12 class, such as G12α and G13α. Examples of β and γ subunits that form trimers with these α subunits include β1 to β5 and γ1 to γ11, respectively.

Examples of G protein-coupled receptor proteins (parenthesized are their respective ligands) are as follows:

(1) Examples of rhodopsin/β adrenaline receptor-like G protein-coupled receptor proteins include BLT1 (leucotriene $B_4$), $ET_A$ and $ET_B$ (encloserine), AT1 (angiotensin), EDG (sphingosine phosphate), CCR and CXCR (chemokine), $α_1$, $α_2$, $β_1$, $β_2$ and $β_3$ (norepinephrine), $M_1$, $M_2$ and $M_3$ (acetylcholine), $5-HT_{1A}$ (serotonin), NK-1 (substance P), $Y_1$ (neuro-peptide Y), $B_1$ and $B_2$ (bradykinin), V1A (basopressin), CB1 and CB2 (anandamide), D1, D2 and D3 (dopamine), odor receptors, MT1, MT2, and MT3 (melatonin) and photoreceptors.

(2) Examples of glucagon/VIP (Vasoactive intestinal peptide)/calcitonin receptor-like G protein-coupled receptor proteins include calcitonin receptors (calcitonin), VIP1, VIP2 (Vasoactive intestinal peptide), CRF1 (corticotropin-releasing factor) and PTH receptors (parathormone).

(3) Examples of metabolic neurotransmitter/calcium receptor-like G protein-coupled receptor proteins include $mglu_1$, $mglu_2$ (glutamic acid), $GABA_B$ (γ-amino butyric acid) and taste receptors (Gether, U. Uncovering molecular mechanisms involved in activation of G protein-coupled receptors. Endocrine Reviews (2000) 21, 90-113) (1998 Receptor and Ion Channel Nomenclature Supplement, Trends in Pharmacological Science, 1998).

In the present invention, at least one type of recombinant baculovirus containing a gene encoding the above-mentioned protein to be expressed is employed.

Baculoviruses which infect insects and cause diseases are envelope viruses having cyclic double stranded DNAs as gene, and shows a sensitivity to insects of the orders Lepidoptera, Hymenoptera, Diptera and the like. Among the baculoviruses, nuclear polyhedrosis virus (NPV) refers to a group which produces a large amount of occlusion bodies called polyhedra within the nucleus of an infected cell. A polyhedron comprises polyhedrin proteins having a molecular weight of 31 kDa, and is produced in a large amount at late stage of the infection and have many viral particles embedded therein. Since polyhedra is essential for the viruses to survive in nature, but unnecessary for the proliferation of a virus, the viruses can infect and proliferate even if a foreign gene to be expressed is inserted in place of a polyhedron gene.

As baculoviruses used in the present invention, a virus vector such as *Autographa californica* NPV (AcNPV) of the subfamily Phytometra and *Bombyx mori* NPV (BmNPV) of silkworm, can be used.

Example of a host of AcNPV (infected and established cells) include *Spodoptera frugiperda* cell (Sf cell), and that of BmNPV (infected and established cells) include BmN4 cell. Vectors of AcNPV line are preferred because Sf cell possesses a higher proliferation rate compared to BmN4 cells and the like, and AcNPV possesses infectivity to human liver cells, human fetal nephrocytes and the like.

As hosts, for example, *Spodoptera Frugiperda* cell lines Sf9 and Sf21 have been established from ovarian tissue of *S. frugiperda* larva and are available from Invitrogen, Pharmingen (San Diego, Calif.), ATCC or the like. In addition, a living insect larva can also be used as a host.

A method for constructing a recombinant virus used in the present invention may be performed by standard techniques, and it can be performed by, for example, the following steps.

First, a recombinant transfer vector is constructed by inserting a gene of a protein to be expressed into the transfer vector.

The whole size of the transfer vector generally ranges from about several kb to about 10 kb where about 3 kb of the size corresponds to a backbone derived from a plasmid, which contains an antibiotic resistance gene (e.g. resistance to ampicillin) and a signal to initiate DNA replication in bacteria. In addition to this backbone, a transfer vector generally contains several kb each of the 5' and 3' regions of a polyhedron gene, so that, when transfection as described below is performed, homologous recombination between the gene of interest and the polyhedron gene occurs between these sequences. Preferably, the transfer vector contains a promoter for the expression of a gene of a protein. Examples of promoters include a polyhedron gene promoter, a p10 gene promoter, and a capsid gene promoter.

Types of transfer vectors are not specifically limited. Examples of AcNPV line transfer vectors include pEVmXIV2, pAcSG1, pVL1392/1393, pAcMP2/3, pAcJP1, pAcUW21, pAcDZ1, pBlueBacIII, pAcUW51, pAcAB3, pAc360, pBlueBacHis, pVT-Bac33, pAcUW1, and pAcUW42/43; those of BmNPV line transfer vectors include pBK283, pBK5, pBB30, pBE1, pBE2, pBK3, pBK52, pBKblue, pBKblue2, pBF series (all of which are available from FUNAKOSHI, Fujisawa Pharmaceutical Co., Ltd. and the like).

Next, in order to prepare recombinant viruses, the above-mentioned recombinant transfer vectors are mixed with viruses, and then transferred into cultured cells to be used as a host, or alternatively are transferred into cultured cells to be used as host which have been previously infected with viruses, so as to cause homologous recombination between the recombinant transfer vectors and viral genome DNAs, thereby constructing recombinant viruses.

Cultured cells used as a host are the above-mentioned host, and generally include insect culture cells (e.g. Sf9 cells, BmN cells, etc.). Culturing conditions are determined appropriately by persons skilled in the art. When Sf9 cells are used, culturing is preferably performed at around 28° C. in a medium containing 10% fetal calf serum. The thus constructed recombinant viruses can be purified by standard techniques such as plaque assay. The thus prepared recombinant viruses can be easily distinguished from non-recombinant viruses since they cannot form polyhedra because of the foreign DNA replaced or inserted in the region of the gene for the polyhedron protein of the nuclear polyhedrosis virus.

In the method of the present invention, the protein of interest can be recovered by allowing the above-mentioned recombinant baculovirus to infect the above-described appropriate host (culture cells of e.g. *Spodoptera Frugiperda* cell lines Sf9 and Sf21 or insect larvae) and recovering extracellular budded virus (BV) from the culture supernatant by separation means such as centrifugation after a certain period of time (e.g. 72 hours). Only one type of recombinant baculovirus may be infected, or two or more types of recombinant baculovirus may be co-infected.

Extracellular budded baculoviruses can be recovered, for example, as described below.

First, a culture solution of the infected cells is centrifuged at 500 to 1,000 g, thereby recovering the supernatant containing extracellular budded baculoviruses. The supernatant is centrifuged at about 30,000 to 50,000 g so as to obtain the precipitate containing extracellular budded baculoviruses. The precipitate is suspended in an appropriate buffer. The virus suspension is applied onto proper concentration gradients (e.g. sucrose sequential gradient), and then centrifuged at 100,000 g for fractionation. Finally, fractions containing desired proteins can be selected from the obtained fractions.

When the expressed proteins are obtained in the form of solubilized proteins, extracellular budded viruses are recovered by centrifugation at e.g. 40000 g from the culture solution of the infected cells. The recovered pellet is suspended in an appropriate buffer, treated with a dissolution agent such as lyso-phosphatidylcholine, and centrifuged at 30,000 rpm, thereby separating the suspension into a supernatant and a precipitate. The solubilized protein of interest is recovered in the supernatant.

The expressed protein recovered by the method of the present invention as described above is characterized in that it is recovered in its active form. Preferably, at least 50% or more, more preferably 60% or more, still more preferably 70% or more, further more preferably 80% or more, still more preferably 90% or more, and particularly preferably 95% or more of the protein is recovered in its active form by the method of the present invention. Such an active form of a membrane protein could not be recovered in a high yield by the conventional methods.

The present invention further provides a method for analyzing an interaction between a membrane-bound receptor protein in a budded baculovirus and a ligand, by using the budded baculovirus released from a host infected with at least one type of recombinant baculovirus which contains a gene encoding an interacting protein and a gene encoding a membrane-bound receptor protein which interacts with said interacting protein to perform its function.

Examples of a method for measuring interaction between a membrane-bound receptor protein and a ligand are not specifically limited, and can be appropriately selected by persons skilled in the art. For example, ligand-binding ability can be measured by using a radio-labeled ligand. Specifically, a budding baculovirus containing a membrane-bound receptor protein is added for reaction to a buffer (e.g., a buffer solution appropriate for binding) containing a ligand labeled with [$^3$H] or the like. The reaction conditions are appropriately determined depending on the type of combination of a receptor and a ligand. After reaction, a reaction solution is filtered and adsorbed to a solid phase carrier such as an appropriate filter so as to stop reaction. The solid phase carrier is washed and dried, so that only complexes are immobilized on the solid phase carrier. Radioactivity of the solid phase carrier is measured by using a scintillation counter, thereby measuring interaction (that is, ligand binding ability) between a membrane-bound receptor protein and a ligand.

The present invention further provides a method for screening a substance which promotes or inhibits an interaction between a membrane-bound receptor protein in the budded baculovirus and a ligand, wherein an interaction between a membrane-bound receptor protein in the budded baculovirus and a ligand is analyzed in the presence of a test substance by using the budded baculovirus released from a host infected with at least one type of recombinant baculovirus which contains a gene encoding an interacting protein and a gene encoding a membrane-bound receptor protein which interacts with said interacting protein to perform its function.

Examples of test substances to be screened include peptides, polypeptides, synthetic compounds, fermented products of microorganisms, extracts from organisms (including plant or animal tissues, microorganisms and cells) or libraries thereof. Examples of libraries include a synthetic compound library (e.g. a combinatorial library) and a peptide library (e.g. a combinatorial library). Chemical substances to be screened may be either natural or synthetic materials. Single candidate chemical substance may be individually tested, or a mixture of candidate chemical substances (including libraries) may be tested. Furthermore, a fractionated mixture such as a cell extract may be screened, followed by repeated fractionation, thereby isolating a substance with a desired activity.

These test substances are preferably those predicted to promote or inhibit interaction between a membrane-bound receptor protein and a ligand.

The screening method of the present invention enables screening an inhibitor or an activating agent for a membrane-bound receptor protein. The present invention also encompasses a substance which is obtained by the screening method of the present invention and promotes or inhibits interaction between a membrane-bound receptor protein and a ligand.

The present invention will be further explained with examples as follows, but the invention is not limited by these examples.

EXAMPLE

Example 1

Preparation of Recombinant Baculovirus which Expresses G Protein Coupled Receptor BLT1 is a receptor for leucotriene $B_4$ ($LTB_4$) produced from arachidonic acid (Serhan, C. N., Haeggstrom, J. Z. and Leslie, C. C. Lipid Mediator Networks in Cell Signaling: Update and Impact of Cytokines. (1996) FASEB J. 10, 1147-1158). BLT1 is a G protein coupled receptor present on a cell membrane, and intracellular signal transduction is caused by specific binding of $LTB_4$ (Yokomizo, T., Masuda, K., Kato, K., Toda, A., Izumi, T. and Shimizu, T. Leukotriene B4 receptor. Cloning and Intracellular Signaling. (2000) Am. J. Respir. Crit. Care. Med. 161, S51-S55).

(1) Culturing and Infection of Cells, and Collection of Budding Baculovirus

A human BLT1 cDNA open reading frame (Yokomizo, T., Izumi, T., Chang, K., Takuwa, Y. and Shimizu, T. A G-protein-coupled Receptor for Leukotriene $B_4$ that mediates Chemotaxis. (1997) Nature 387, 620-624) was subcloned into a pBlueBac4.5™ vector (Invitrogen, Carlsbad, Calif.) or a pBlueBacHis2A vector, thereby producing pBlueBac-BLT1 and pBluBac-His-BLT1, respectively. Sf9 cells (Invitrogen) were sub-cultured in a complete medium (Grace's supplemented media (GIBCO BRL) containing 10% fetal calf serum (Sigma), 100 units/ml penicillin and 100 μg/ml streptomycin) on a 10 cm dish at 27 C.°. Large scale culturing was performed in a 1 L spinner flask (Wheaton) containing a complete medium supplemented with 0.001% pluronic F-68 (GIBCO BRL). To prepare a recombinant baculovirus, Sf9 cells were co-infected with Bac-N-Blue DNA (derived from ApMNPV) and pBlueBac-BLT1 or pBluBac-His-BLT1 according to the instruction (Bac-N-Blue™ Transfection Kit, Invitrogen).

(2) ELISA Analysis of Expression of Receptor in Budding Baculovirus

Sf9 cells were cultured in a volume of 500 ml in a 1 L spinner flask (Wheaton) at a concentration of $2 \times 10^6$ cells/ml. The cells were infected with the recombinant viruses produced in (1) above at MOI=5, and then the culture solution at 72 hours after infection was used for a subsequent experiment. The culture solution was centrifuged at 1,000×g for 10 minutes, and was separated into a precipitate and a supernatant. The precipitate was suspended in a cell disruption buffer (20 mM Tris-HCl pH 7.4, 0.25 M sucrose, 10 mM $MgCl_2$, 1 mM EDTA, 0.5 mM PMSF, 2 mM DTT), subjected to ultrasonication, and then centrifuged at 10,000×g for 30 minutes. The supernatant was ultra-centrifuged at 100,000×g for 1 hour, and then the resulting precipitate was suspended in a phosphate buffer (PBS), thereby obtaining a cell membrane fraction. The supernatant resulting from centrifugation at 1,000×g was centrifuged at 10,000×g for 15 minutes, followed by centrifugation of the supernatant at 45,000×g for 30 minutes. Then, the precipitate was suspended in PBS, centrifuged at 45,000×g for 30 minutes. The precipitate was suspended in PBS, thereby obtaining budding virus fractions (BV fractions).

The expression amount of BLT1 in the BV fractions was confirmed by ELISA using anti-BLT1 anti-sera (Cayman) which recognize the C-terminus of the receptor (FIG. 1). As a result, binding of antibodies to the expressed receptors was confirmed in the BV fractions with 100 ng or more of protein quantity, compared to a case when cells were infected with a wild type baculovirus.

Figure 2:
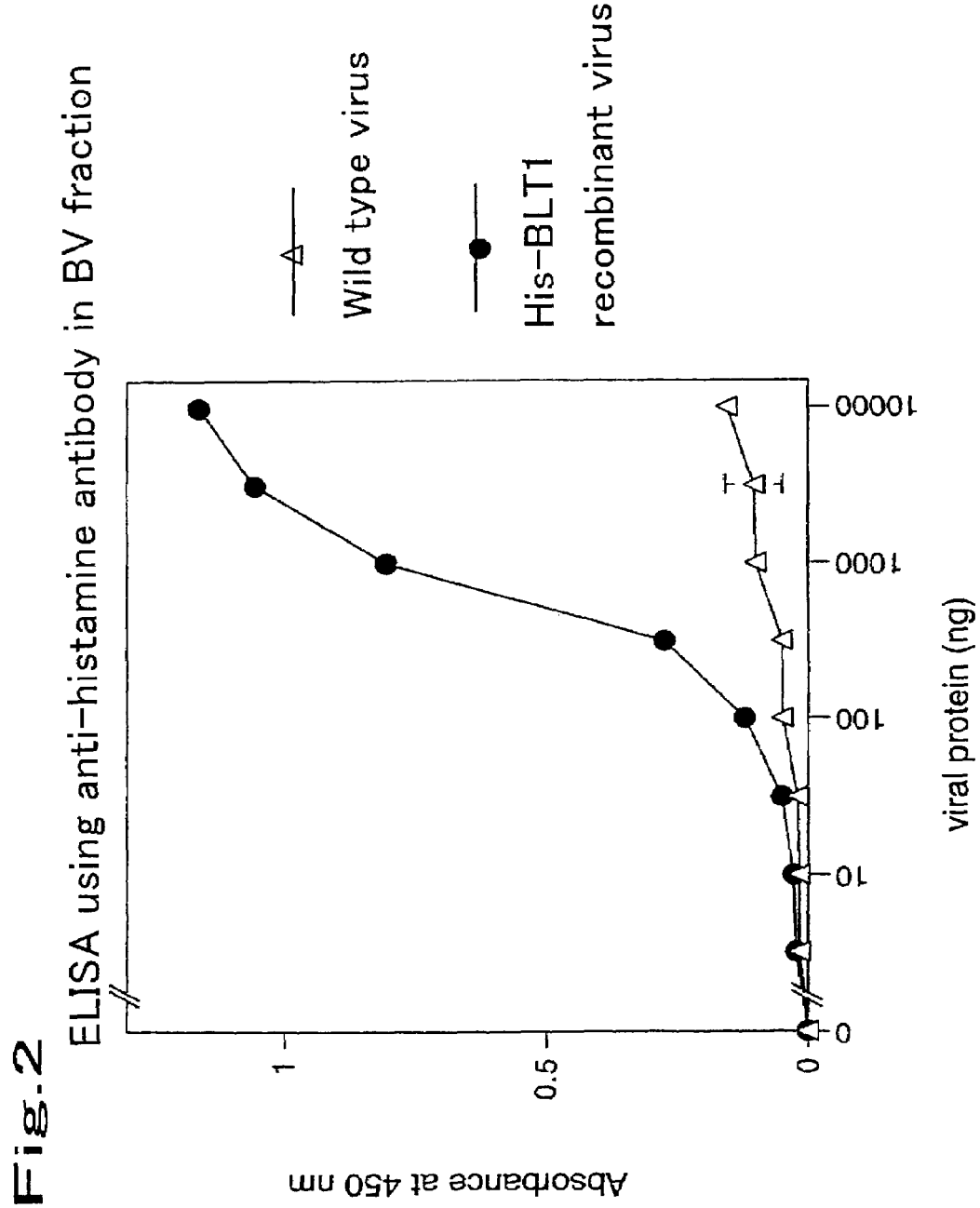
FIG. 2 shows the result of ELISA using anti-histamine antibody in BV fraction.

Further, in the case of ELISA using anti-His-tag antibodies was performed for the BV fractions of expressed receptors containing His-tag fused to the N-terminus, similar results were confirmed (FIG. 2).

Culture solution of Sf9 cells infected with the recombinant virus was collected every 24 hours during 0 to 96 hours. Cell membrane fractions and supernatants following centrifugation at 1,000×g for 10 minutes were centrifuged at 10,000×g for 10 minutes, thereby preparing supernatants (supernatant fractions). Then, changes with time in the expression amount of the receptor were confirmed (FIG. 3). Using 1 μg of the cell membrane fraction and 200 μl of the supernatant fraction at each time point, ELISA was performed with anti-BLT1 anti-sera. Thus, the cell membrane fractions started to show the expression of the receptor at 48 hours after culturing, and the supernatant fractions started to show the expression of the receptor at 72 hours after culturing. These results suggest that the virus containing the receptor is expressed in the culture solution after 72 hours.

The expression amount of the receptor of the BV fraction and that of the cell membrane fraction were compared by ELISA using anti-BLT1 anti-sera (FIG. 4). With a protein quantity of 1 μg in each case, the expression amount of the receptor in the BV fraction was about a half of that in the cell membrane fraction.

(3) Analysis on Binding Activity of Ligand to Receptor in Budding Baculovirus

The binding activity of ligands in the BV fraction and the cell membrane fraction were confirmed by an experiment for the binding of $[^3H]LTB_4$ to each sample (FIG. 5). The experiment for the binding of $[^3H]LTB_4$ was performed by adding the BLT1BV fraction or the cell membrane fraction to a binding buffer containing $[^3H]LTB_4$ (50 mM Tris-HCl pH 7.4, 10 mM $MgCl_2$, 10 mM NaCl, 0.1% fatty acid-free BSA) to prepare 200 μl of a reaction solution, and allowing the solution to stand for 1 hour at room temperature. The reaction solution was filtered through a GF/C glass microfiber filter (Whatman) for adsorption to stop reaction. Then, the filter was washed three times with 2 ml of an ice-cooled binding buffer, and was dried. Then, radioactivity was measured by using a scintillation counter. Non-specific binding was calculated by adding 10 μM of $LTB_4$ into the reaction solution.

The binding amount of $[^3H]LTB_4$ to BLT1- or His-tag BLT1-expressing BV fraction was approximately 3 to 4-fold greater than that of each receptor-expressing Sf9 cell membrane fraction. The above (2) and this result indicate that receptors capable of binding to ligands were expressed with a higher proportion in the BV fractions than in the cell membrane fractions.

Example 2

Co-Expression of G Protein Coupled Receptor and G Protein in Budding Baculovirus BLT1 is coupled intracellularly with Gi-like or some Gq-like G proteins, followed by specific binding of $LTB_4$, so that the coupled G proteins are activated (Gaudreau, R, Gouill, C. L., Metaoui, S., Lemire, S., Stankova, J. and Rola-Pleszczynski, M. Signalling through the leukotriene $B_4$ receptor involves both αi and α16, but not αq or α11 G protein subunits (1998) Biochem J. 335, 15-18). It has been reported that G proteins expressed in Sf9 cells are mainly Gs-like and Gq-like G proteins, and the expression amount of Gi-like G-proteins is low (Obosi, L., Schuette, D. G., Europe-Finner, N., Beadle, D. J., Hen, R., King, L. A. and Bermudez, I. Functional characterization of the *Drosophila* 5-HT$_{dro1}$ and 5-HT$_{dro2B}$ serotonin receptors in insect cells: activation of a Gαs-like protein by 5HT$_{dro1}$ but lack of coupling to inhibitory G proteins by 5-HT$_{dro2B}$. (1996) FEBS Lett. 381, 233-236).

(1) Comparison of Expression Amount of Receptor in the Co-Expression of G Proteins 200 ml of Sf9 cells at a concentration of $2 \times 10^6$ cells/ml was infected, at MOI=2 per virus, with each of rat G protein subunits α and β, γ (Gαi1, Gβ1, Gγ2)-recombinant viruses, and with His-tag BLT1-expressing recombinant virus. 72 hours later, BV fractions were prepared, and then the expression of receptors was confirmed by ELISA using anti-BLT1 anti-sera (FIG. 6). The expression amount of receptors in the BV fractions was the highest in the cells infected with the receptor-expressing recombinant viruses only, and followed by those infected with the Gαi1 recombinant viruses in addition to receptor-expressing recombinant viruses, those infected with Gβ1 and Gγ2 recombinant viruses in addition to receptor-expressing recombinant viruses, and those infected with Gαi1 and Gβ1, Gβ2 recombinant viruses in addition to receptor-expressing recombinant viruses, in decreasing order. These results suggest that the expression amount of receptors decreased as the number of virus types for infection increased in the case of co-infection with receptor- and G protein-expressing recombinant viruses respectively at MOI=2.

Further, infection with only recombinant virus of G proteins (Gαi1, Gβ1, Gγ2) resulted in binding of antibody at low level which is equivalent to that of infection with wild type baculoviruses.

(2) Comparison of Ligand Binding Ability in the Co-Expression of G Proteins 200 ml of Sf9 cells at a concentration of $2 \times 10^6$ cells/ml was infected, at MOI=2 per virus, with each of rat G protein subunits α and β, γ (Gαi1, Gβ1, Gγ2)-recombinant viruses, and with His-tag BLT1-expressing recombinant viruses. 72 hours later, BV fractions were prepared, and then the effect of co-expression of G proteins on ligand binding ability was confirmed by an experiment for binding of ligands as shown in Example 1(3) (FIG. 7).

0.25 nM [$^3$H]LTB$_4$ binding ability at 0.3, 1 or 3 μg of the BV fraction was the highest in the cells co-infected with His-tag BLT1-expressing recombinant viruses and rat G protein subunits α and β, γ (Gαi1, Gβ1, Gγ2), followed by those co-infected with the receptor- and Gαi1 recombinant viruses, and those co-infected with the receptor- and Gβ1, Gγ2 recombinant viruses, in decreasing order. Further, ligand-binding activity of the cells co-infected with the receptor- and Gβ1, Gγ2 recombinant viruses was the same as that of the cells co-infected with the receptor-expressing recombinant viruses only. These results confirmed that co-expression of G protein α subunit results in increased ligand binding activity of receptors, and co-expression of G protein subunits α and β, γ results in the highest ligand binding activity.

Binding activity of [$^3$H]LTB$_4$ at a concentration ranging from 0 to 2 nM to 0.3 μg of the receptor-expressing BV fraction was confirmed (FIG. 8). Co-expression of the receptors and G protein subunits α and β, γ resulted in increased binding ability at a low ligand concentration, as compared with the expression of receptors only. The result suggests that co-expression of receptors and G protein subunits α and β, γ in the BV fraction causes the expressed receptors to bind with high affinity to ligands.

INDUSTRIAL APPLICABILITY

The present invention enables expression of a membrane-bound receptor which functions by forming a complex, such as GPCR and T cell receptor. The membrane-bound receptor can be used for screening a substance which inhibits or imitates binding or signal transduction.

What is claimed is:

1. A method for expressing a leukotriene B4 receptor which comprises culturing a host infected with at least one recombinant baculovirus which contains a gene encoding an interacting protein and a gene encoding a leukotriene B4 receptor protein which interacts with said interacting protein, and co-expressing said interacting protein and said leukotriene B4 receptor protein in a budded baculovirus released from said host, and either (1) recovering a budded baculovirus released from said host, (2) recovering supernatant containing a budded baculovirus released from said host, or (3) a combination thereof, wherein the interacting protein comprises rat G protein subunits α, β, and γ, and wherein the host is an insect cell or an insect larva.

2. The method of claim 1 which comprises culturing a host infected with at least one recombinant baculovirus which contains a gene encoding an interacting protein and at least one recombinant baculovirus which contains a gene encoding a leukotriene B4 receptor protein which interacts with said interacting protein, and co-expressing said interacting protein and said leukotriene B4 receptor protein in a budded baculovirus released from said host.

3. A method for preparing a physiologically active leukotriene B4 receptor protein which comprises culturing a host infected with at least one recombinant baculovirus which contains a gene encoding an interacting protein and a gene encoding a leukotriene B4 receptor protein which interacts with said interacting protein, and recovering a budded baculovirus released from said host, wherein the interacting protein comprises rat G protein subunits α, β, and γ, and wherein the host is an insect cell or an insect larva.

4. The method of claim 3 which comprises culturing a host infected with at least one recombinant baculovirus which contains a gene encoding an interacting protein and at least one recombinant baculovirus which contains a gene encoding a leukotriene B4 receptor protein which interacts with said interacting protein, and recovering a budded baculovirus released from said host.

5. A method for analyzing an interaction between a leukotriene B4 receptor protein in a budded baculovirus and a ligand, wherein the budded baculovirus is released from a host infected with at least one recombinant baculovirus which contains a gene encoding an interacting protein and a gene encoding a leukotriene B4 receptor protein which interacts with said interacting protein, and co-expressing said interacting protein and said leukotriene B4 receptor protein in a budded baculovirus released from said host, and wherein the method comprises adding the budded baculovirus and a ligand and measuring ligand binding to the leukotriene B4 receptor protein, and wherein the interacting protein comprises rat G protein subunits α, β, and γ, and wherein the host is an insect cell or an insect larva.

6. A method for screening a substance which promotes or inhibits an interaction between a leukotriene B4 receptor protein in a budded baculovirus and a ligand, wherein the budded baculovirus is released from a host infected with at least one recombinant baculovirus which contains a gene encoding an interacting protein and a gene encoding a leukotriene B4 receptor protein which interacts with said interacting protein, and co-expressing said interacting protein and said leukotriene B4 receptor protein in a budded baculovirus released from said host, and wherein the method comprises analyzing an interaction between a leukotriene B4 receptor protein in the budded baculovirus and a ligand in the presence of a test substance by using the budded baculovirus, and wherein the interacting protein comprises rat G protein subunits $\alpha$, $\beta$, and $\gamma$, and wherein the host is an insect cell or an insect larva.

7. The method according to claim 6, wherein binding affinity of ligand to the leukotriene B4 receptor coexpressed with $\alpha$, $\beta$, and $\gamma$ subunits of the G protein is higher than binding affinity of ligand to the leukotriene B4 receptor expressed without the G protein $\alpha$, $\beta$, and $\gamma$ subunits.

* * * * *